(12) United States Patent
Langer

(10) Patent No.: US 11,013,336 B2
(45) Date of Patent: May 25, 2021

(54) KYPHOSIS BACK CUSHION DEVICE

(71) Applicant: Victoria Aileen Langer, Mansfield, OH (US)

(72) Inventor: Victoria Aileen Langer, Mansfield, OH (US)

( * ) Notice: Subject to any disclaimer, the term of this patent is extended or adjusted under 35 U.S.C. 154(b) by 199 days.

(21) Appl. No.: 16/112,581

(22) Filed: Aug. 24, 2018

(65) Prior Publication Data

US 2020/0060428 A1     Feb. 27, 2020

(51) Int. Cl.
*A47C 20/02*     (2006.01)
*A61F 5/01*     (2006.01)

(52) U.S. Cl.
CPC .............. *A47C 20/027* (2013.01); *A61F 5/01* (2013.01)

(58) Field of Classification Search
CPC ................................ A47C 20/027; A61F 5/01
USPC ............................................................. 5/632
See application file for complete search history.

(56) References Cited

U.S. PATENT DOCUMENTS

| | | | | |
|---|---|---|---|---|
| 2,835,905 A | * | 5/1958 | Tomasson | A47G 9/10 5/632 |
| 3,333,286 A | * | 8/1967 | Biolik | A47G 9/10 5/632 |
| 3,382,510 A | * | 5/1968 | Robinson | A47C 20/026 5/632 |
| D298,992 S | * | 12/1988 | Voss | 5/638 |
| 5,210,894 A | * | 5/1993 | Minton | A47G 9/10 5/636 |
| D337,914 S | * | 8/1993 | McDonald | 5/638 |
| 5,503,459 A | * | 4/1996 | White | A61G 5/12 297/440.2 |
| 5,647,076 A | * | 7/1997 | Gearhart | A47C 20/025 5/631 |
| 6,360,388 B2 | | 3/2002 | Langer | |
| 6,637,058 B1 | * | 10/2003 | Lamb | A61G 13/12 5/638 |
| 7,444,698 B2 | * | 11/2008 | Jackson, III | A47G 9/1027 5/638 |

(Continued)

OTHER PUBLICATIONS

Ostomy Wound Management, Feb. 2018, vol. 64, Issue 2, p. 38 "Factors Affecting Wound Healing in Individuals With Pressure Ulcers: A Retrospective Study".

(Continued)

*Primary Examiner* — Myles A Throop
(74) *Attorney, Agent, or Firm* — Jacob M. Ward; Ward Law Office LLC

(57) ABSTRACT

A back cushioning device is configured for pressure redistribution each of a cervical region, a thoracic region, a lumbar region, a sacral region, and a coccyx region of a spine of an individual with a medical condition or deformity. The back cushioning device includes a cushioning support matrix with a first end configured to be disposed adjacent to the cervical region of the individual and a tapered second end configured to be disposed adjacent to the coccyx region of the individual. A vertical channel is formed along a length of the cushioning support matrix. The vertical channel is spaced apart from the first end and extends to the second end of the cushioning support matrix. The vertical channel is configured to receive the spine of the individual. A horizontal channel is formed along a width of the cushioning support matrix, the horizontal channel is perpendicular to the vertical channel.

12 Claims, 3 Drawing Sheets

(56) References Cited

U.S. PATENT DOCUMENTS

| | | | | |
|---|---|---|---|---|
| D625,420 S | * | 10/2010 | Sharps | D24/184 |
| 8,006,335 B1 | * | 8/2011 | Andermann | A61G 7/07 5/632 |
| 8,069,515 B1 | * | 12/2011 | Tingey | A47G 9/10 5/632 |
| 8,566,987 B1 | * | 10/2013 | Burge | A47C 27/15 5/655.9 |
| 9,138,087 B2 | * | 9/2015 | Mobley | A47G 9/1054 |
| 10,052,223 B2 | | 8/2018 | Turner | |
| 2004/0160111 A1 | * | 8/2004 | Koffler | A47C 7/029 297/452.25 |
| 2007/0199646 A1 | * | 8/2007 | Wycech | A47C 27/15 156/242 |
| 2009/0320208 A1 | * | 12/2009 | Mandelzis | A47C 20/026 5/632 |
| 2012/0037163 A1 | * | 2/2012 | Jones | A47C 20/027 128/845 |
| 2012/0186025 A1 | * | 7/2012 | Kardos | A47C 20/027 5/655.9 |
| 2013/0305456 A1 | * | 11/2013 | Thompson | A61G 13/1255 5/632 |
| 2016/0000242 A1 | * | 1/2016 | Campagna | A61G 13/122 5/632 |
| 2019/0231577 A1 | * | 8/2019 | Okamoto | A61F 5/028 |

OTHER PUBLICATIONS

No. 15, Treatment of Pressure Ulcers, US Department of Health & Human Services, Dec. 1994, p. 42.

H. Fred Moseley M.A., D.M., M.Ch. (Oxon) "Disorders of the Vertebral Column", Textbook of Surgery, Third Edition, The C.V. Mosley Company 1959, St. Louis USA, p. 1244.

Robert H. Goebel, MD JD, Clinical Practice Guidelines for Pressure Ulcer Prevention can Prevent Malpractice Lawsuits in Older Patients, Elsevier Journal of WOCN, Jul. 1999, Paragraph 2 Under Setting and Subjects.

* cited by examiner

KYPHOSIS BACK CUSHION DEVICE

BACKGROUND

The spine of the human anatomy is made up of 33 uniquely individualized bones, comprised of 5 regions. The regions are the cervical (7), thoracic (12), lumbar (5), sacral (5) and coccygeal (4), stacked one on top of the other (Textbook of Surgery, Third Edition-Edited by H. Fred Moseley, M.A., D.M., M.Ch. (Oxon), F.A.C.S., F.R.C.S (Eng.) F.R.C.S. (C)) said the spinal column provides the main support for your body, allowing you to stand upright, bend, and twist, while protecting the spinal cord from injury. Strong muscles and bones, flexible ligaments and tendons, and sensitive nerves contribute to a healthy spine. However, any of these structures that are affected by strain, injury or disease can cause pain. When a healthy spine is viewed from the side in an adult it has a natural slight concave curve, the thoracic and sacral regions have a gentle convex curve. In a human with an abnormal shaped spine, i.e. abnormal curve of the upper spine which is known as a medical condition called thoracic spine kyphosis or in layman terms "hunchback". Upon viewing a kyphotic human, the front of the thoracic spine is crushed, that segment of the spine tips forward, resulting in an excessive kyphotic curve and forward stooped posture. Treatment typically will address the underlying osteoporosis (to prevent future fractures) as well as pain reduction and possibly surgical repair. The upper back, or thoracic region of the spine, is meant to have only a slight natural curve. The spine is a bony prominence in itself. In a very kyphotic condition or a very sharp protruding curve to the spine it is evident you can visually see the curved arched back and many disks with a very thin layer of tissue covering the bony prominence of the spine. At risk also for a kyphotic condition are post-menopausal females as they age. Gravity over time and as we age places force on the entire spine thus the spine becomes weakened and will curve and protrude even further putting great pressure on each disk and the bony prominence's causing them to protrude. Bony prominences are any bony protrusion such as the occipital bones on the back of the head, hips, knees, ischial tuberosities which are your sitter bones, or the spine which is what totally supports our entire human skeletal frame. With prolonged pressure or gradients on the tissue of the skeletal frame of our body it may become uncomfortable and may be painful due to this prolonged pressure. Pressure gradients are where one's blood vessels, muscle, subcutaneous fat and skin are compressed between bone and a lying or sitting surface, pressure is transmitted from the body surface toward the bone. The external surface produces pressure and the bone produces counter pressure. These said opposing forces result in a cone-shaped pressure gradient (Pressure Ulcers-Guidelines for Prevention and Nursing Management, Second Edition). All of the tissue between the external surface and the skeletal anatomy is involved. The brain may or may not send a signal of discomfort to the skeletal muscles calling for movement. In most healthy humans, this message would require them to move and cause blood flow, nutrients and oxygen back into the spine and the bony prominences; however, with many patients or persons who are medically compromised the signal never gets through thus causing a vast amount of pressure on the spine and each bony prominence. Without addressing this condition and left unattended the prolonged pressure on the soft tissue will cause decreased oxygenation, nutrition and blood flow thus leading to hypoxia eventually leading to necrotic tissue and causing a decubitus ulcer i.e. pressure injury (Pressure Ulcer Treatment, Quick Reference Guide for Clinicians, Number 15—AHRQ and NPUAP Guidelines).

Prolonged pressure has a profound effect on the soft tissues. All of the tissue between the external surface and the skeletal anatomy is involved. However, the greatest tissue destruction is beneath the skin surface at the bony interface. If left undisturbed this decreased circulation to the area can drive the oxygen tension of the region into a state of hypoxia and eventually necrosis. The necrotic area can then rupture into a wound that begins inside the body and erodes to the outside. These are often referred to as "pressure injuries" (NPUAP, AHRQ Guidelines National Pressure Ulcer Advisory Panel). If left untreated a Stage IV (NPUAP, AHRQ) pressure injury can in some cases lead to death with a condition known as osteomyelitis.

Healthy individuals are rarely affected with pressure ulcers because they have the feeling and sensation to move and reposition. In a kyphotic, paraplegic, post-surgical stenous surgery patient they may have limited mobility, insufficient oral nutrition, low hemoglobin levels, low MAP (Ostomy Wound Management, February 2018, Vol. 64, Issue 2) and at risk for a pressure injury. In any of these cases the bony prominence of the spine must be off loaded properly with true pressure relief and to maintain that no further pressure is put on the bony prominences of the spine thus causing a pressure injury.

In the medically compromised individual who is admitted into a hospital or long-term care setting and is absolutely immobile or cannot turn themselves the government has set forth the NPUAP, AHRQ guidelines that nursing students are educated during their schooling on how important the turning cycle of a physically compromised patient/person can be with pressure on the bony prominences and the severe outcome of a pressure injury if these guidelines are not followed.

Offloading is a medical necessity to prevent pressure ulcer formation. The repositioning of the body is effective for many patients but for some patients repositioning is not an option. Patients/persons in the end stage of life, traction patients, burn patients or patients/persons that are confined to being immobile. Although regular scheduled repositioning may not be an option, many patients are susceptible to the formation of pressure injuries. Protecting patients/persons from the development of pressure injuries involves monitoring pressure points and making sure persistent pressure contact on bony prominences does not occur by providing pressure redistribution and true pressure relief. This may be done by moving the patient/person to reposition body weight on another part of the body at regular time schedules based on the NPUAP and AHRQ guidelines (Pressure Ulcer Treatment, Quick Reference Guide for Clinicians, Number 15—AHRQ and NPUAP Guidelines). For example, the bony prominence of the trochanter i.e. (hip), ischial tuberosity's (sitter bones) or spine may be a point where a pressure injury may develop. By repositioning on a regular basis, one can often times be successful in preventing tissue hypoxia from occurring.

Studies indicate that comprehensive prevention programs are effective in reducing incidence rates and can be cost effective. Thus, prevention is crucial to reduce overall health costs (AHRQ, Agency for Healthcare Research and Quality-Preventing Pressure Ulcers in Hospitals, a Toolkit for Improving Quality of Care). In the U.S. 2.5 million patients develop pressure ulcers each year. Pressure ulcers cost $9.1-11.6 billion per year to the US health care system. The cost of individual patient care ranges from $20,900 to 151,700 per pressure ulcer. Medicare estimated in 2007 that each pressure ulcer added $43,180 in costs to a hospital stay. More than 17,000 lawsuits are related to pressure ulcers annually. It is the second most common claim after wrongful death and greater than falls or emotional distress (Goebel et al, Clinical Practice Guidelines for pressure ulcer prevention can prevent lawsuits in older patients. JWOCN). In a study of the impact of compliance on medical malpractice awards: 35 Plaintiffs were awarded $14,418,770. Had health care defendants followed guidelines $11,389,989 might have been saved in 20 lawsuits in addition to the plaintiffs pain and suffering from resulting pressure injuries/ulcers.

Turning a patient/person or offloading a pressure point is simplistic in concept but can be problematic in making sure that the patient/person remains in the desired position. Nursing care often use pillows or blankets rolled in such a way to "pack" in around the patient/person to assist in maintaining the desired position. Whilst these approaches have some utility they are not always useful for offloading the weight. In fact, in some cases pillows and blankets packed too tightly lead to the very complication that they were intended to alleviate. To better serve the patients'/persons' needs and to facilitate offloading of pressure more uniformly, products such as the Global Medical Foam, Inc. (Langer, U.S. Pat. No. 6,360,388) positioning devices have been developed. These devices are cushioning for the body region and have unique designs that ensures a more even distribution of weight over the device. The devices are constructed of polyurethane foam with a solid foam core for rigidity surrounded by a softer foam layer uniquely cut so that it projects foam fingers outwardly from the core. The fingers compress and bend in such a way that the pressure loading is very evenly distributed over a much larger area of the body and the core center is intended to support the body weight. Moreover, because of the unique finger projects they can be wedged in place to very adequately and comfortably support patients/persons in an offload position and in some cases can decrease the frequency for skilled nursing to assist in repositioning.

There are many examples of devices that have design features and material choices for aiding in the offloading of areas of the anatomy. Synthetic and natural rubberized materials are commonly used for this purpose primarily because they are generally soft to the touch and naturally provide some cushioning. Open and closed cell foams such as those formed of polyurethane are commonly used. Other foams are composed of natural latex or polyvinyl materials. Collectively these are elastomeric foams. All foams can be evaluated and given an RMA Value (Rubber Manufacturers of America) which relates to the cushioning or softness of the foam. Ideally the foam of choice is one that is constructed of sufficient elasticity, flexibility, conformability and etc. so that it distributes weight but does not bottom out when it is used to support the anatomy. In most cases the combination of device design and the cushioning index of the material used in its construction combine to provide some utility of design.

Several other inventors have proposed improvements over the solid back support of a cushion or device. In one such improvement Turner (Turner et al, U.S. Pat. No. 10,052,223 B2) describing a garment worn on the upper body provided with a back-support system that can be selectively actuated as needed. However, while providing good offloading capabilities, this invention is only providing pressure relief to the lower back or lordosis area. It does not allow for versatility of offloading the entire spine. Offloading is in a fixed location only and very limited. White (White et al, U.S. Pat. No. 5,503,459 was a similar concept of offloading the spine, this invention has only been able to provide offloading in the thoracic area and as it is a fixed back attached to a wheelchair, this then becomes limited to not only the thoracic area but also to the size and height of a person's anatomical anatomy.

All of these inventions substantially improved the ability to offload limited designated areas of the spine. However, these devices do address pressure relief but neither have addressed pressure redistribution of blood flow and capillary refill time based on NPUAP guidelines of 14,15 (Quick Reference Guide for Clinicians, Number 15-Pressure Ulcer Treatment). 22 mmHG at the arteriolar end and 12 mmHG at the venous end. In providing true pressure relief with the current invention on the market they do not address the entire spine. They address either thoracic or lordosis (White et al, U.S. Pat. No. 5,503,459 and Turner et al, U.S. Pat. No. 10,052,223 B2) In addition, current products on the market have a design of a large square box opening that can cause demarcation and breakdown of tissue in the scapula area. These devices address the need for managing to offload only certain areas of the spine. Neither can offload the complete spine and offer true pressure relief and pressure redistribution. There has been a need for a product that will completely offload the entire spine, but will provide good pressure redistribution of the rest of the back area. The ideal device would not be a fixed stationary device, it would meet the AHRQ and NPUAP guidelines to provide true pressure relief for the entire spine—cervical, thoracic, lumbar, sacral and coccygeal area. It would be tapered at the bottom and to not make the patient/person feel as if they are being pushed forward and falling out of their chair/seat. This device would be universal as to where the device could be used as in a seat, wheelchair, airplane, train in the sitting position and it also would be devised so that a person could use it in the supine, i.e. lying down position as in a bed, on a couch, surgery and/or x-ray table, etc. The ideal device would incorporate all these requirements that are mandated by healthcare facilities regarding pressure relief, pressure redistribution and at the same time addressing the comfort need of an individual. This device would meet the AHRQ/NPUAP guidelines for addressing pressure offloading and pressure relief for prevention and treatment of pressure injuries. It will meet the needs of post spine surgery procedures while offloading properly. It would also be offered in a standard size but could be manufactured in sizes for bariatric patients/persons as in most chair sizes are larger after a standard 250 lb. weight capacity.

SUMMARY

The invention of this application is to provide a pressure relieving and pressure redistribution positioning back cushion that will allow the entire spine to float freely while providing pressure redistribution to the back and scapula's to prevent pressure injury and pressure gradients on the spine. (AHRQ/NPUAP, Number 15-Pressure Ulcer Treatment), the salient feature of this invention is that it is designed to completely offload with true pressure relief of the entire spine addressing all 5 regions in the spinal column. This offloading device would conform comfortably to the back and will allow the spine to have true pressure relief with a vertical cutout through the cushion to allow the spine to float. In addition to this cutout there would also be a second horizontal cutout completely through the offloading pressure relief device to allow the human anatomy to conform better and to add support to this device and application. Thus, the entire cutout would look like a cross and allow zero pressure on the bony prominences of the spine. This device would be of a soft but supporting material that then would be made to comfortably support and offload the spinal column. Materials and or fabrics along with polyurethane foam provide a uniformly soft type of feel that is often used in medical applications, mattresses, pillows, support and positioning devices.

The present invention will allow the spine of the severely kyphotic patient or person to completely float the spine, thus providing true pressure relief, and at the same time provide pressure redistribution to maintain healthy tissue on the back and scapula's. Thus, decreasing the risk of being presented with hypoxia or a pressure injury. The offloading device would also be tapered at the bottom to allow the patient to not feel like they were being positioned near the front of their seat but will allow for the spine to fit completely in the vertical cutout for true pressure relief. The present invention overcomes the limitation by being able to address and provide at all times 5 regions—cervical, thoracic, lumbar, sacral, and coccyx with true pressure relief and pressure redistribution. (AHRQ/NPUAP, Number 15—Pressure Ulcer Treatment)

The present invention was found to be useful not only in a home care setting but also of a medical necessity in many areas of acute and long-term care to offload the entire spine. In addition to daily needs either in a wheelchair, chair, or bed it was found to be of great value during an Mill, CT, X-Ray and Ultrasound procedures. It was also noted to be very useful on the O.R. (Operating Room) table for very kyphotic patients.

The present invention was found to be universal in the application of ease of use, portability and placement whether it be in a wheelchair, chair, bed, automobile, train, bus, airplane, etc.

This present invention could be made of material such as foam, Visco foam, gel, plastic, fiber, rubber, or synthetic fiber.

This device would have a utilitarian and design in a clinical and home care application.

DETAILED DESCRIPTION

Figure 1:
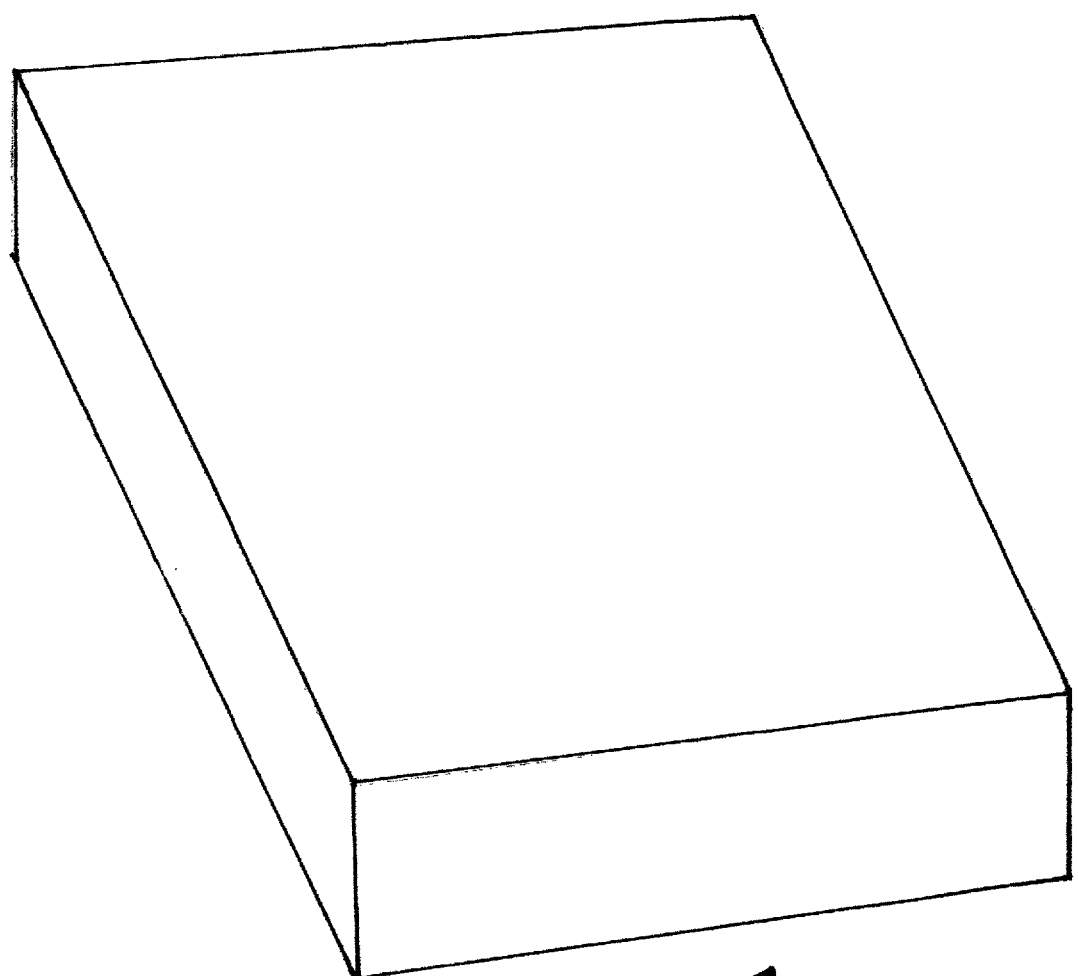
FIG. 1 depicts a block of polyurethane foam cut into an appropriate size for the human anatomy.
Figure 2:
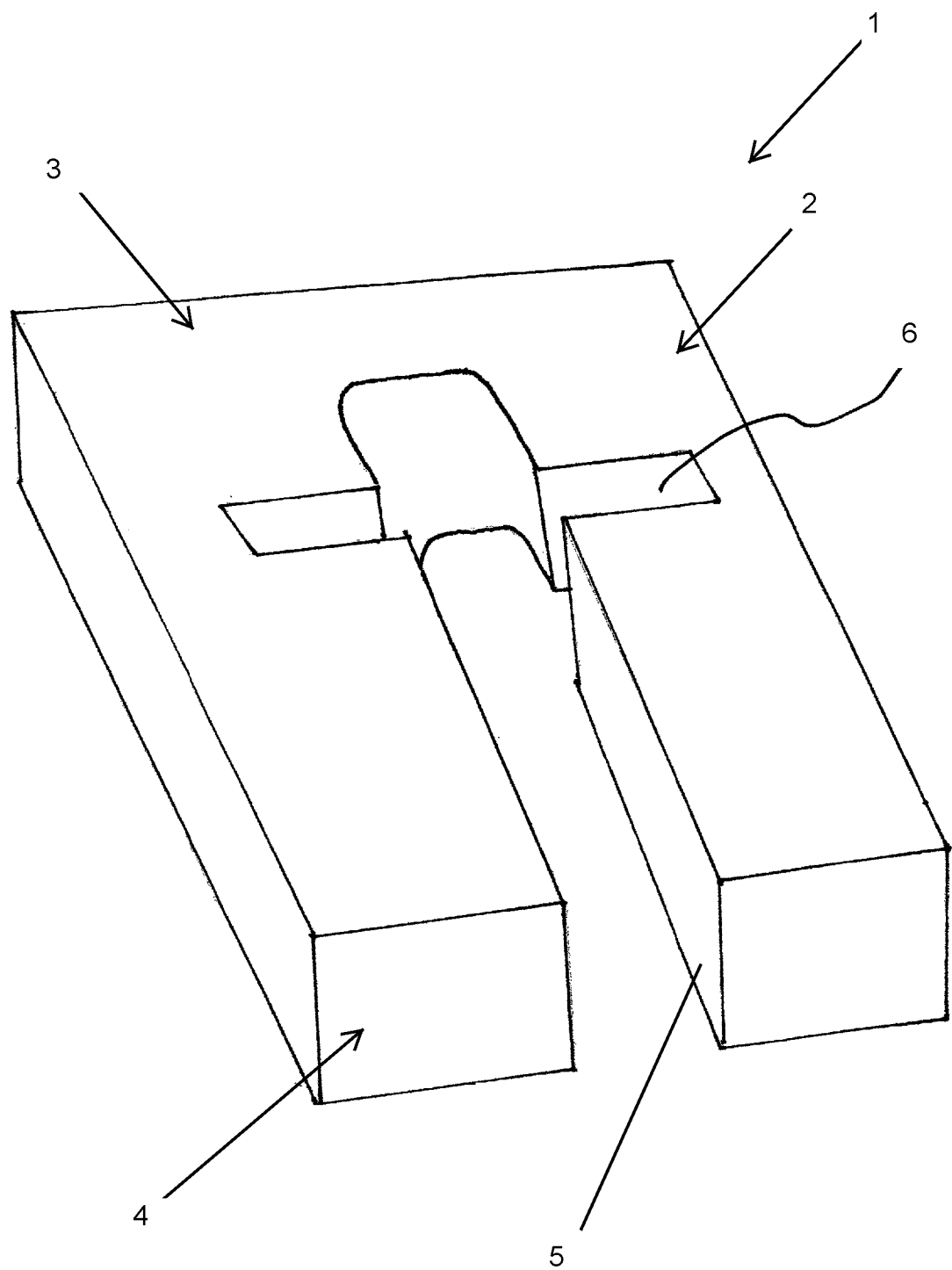
FIG. 2 depicts a block of foam that has been cut into an appropriate shape for a back cushioning device further depicting a vertical channel and a horizontal channel.
Figure 3:
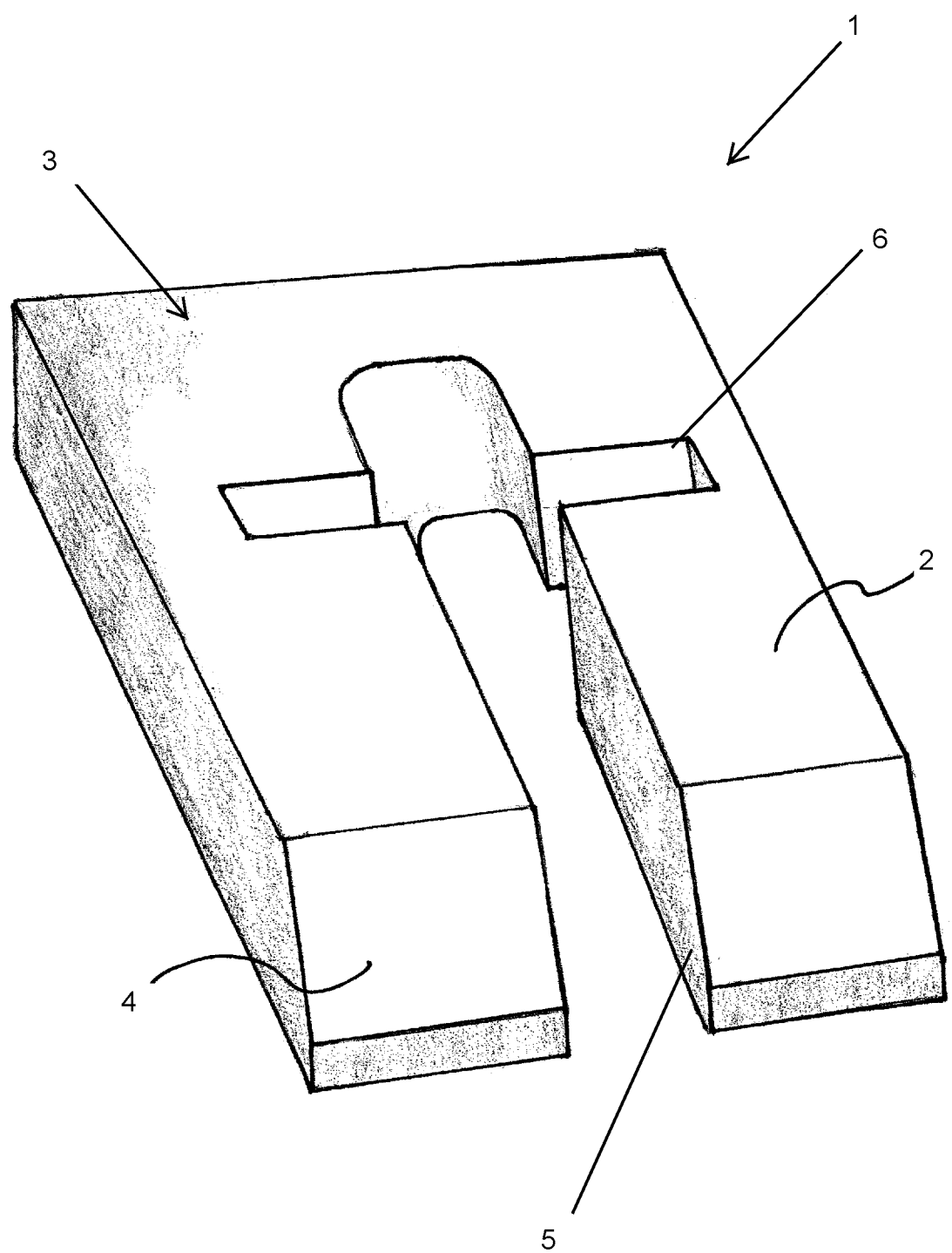
FIG. 3 illustrates a tapered end of the device.

The device of the invention is composed of a cushioning support matrix such as a polyurethane foam or other such elastomeric foams. In all cases of this invention the foam may be generally cut to a size and shape suitable for its intended application. For example, a wheelchair cushion device would be cut to a shape and form that is appropriate to fit that application, might it be a standard size wheelchair 16×18 or it would be cut to fit in a bariatric oversized chair, which could have many sizes. For example, a block of foam would be cut in any suitable manner such as by the use of a foam cutting knife or hot wire. If the device was intended for use in a standard or bariatric wheelchair, regular sitting chair, bed, MM, CT, X-Ray, and/or the O.R. table for offloading during surgery then the foam or materials used would be cut to an appropriate size to fit that application or procedure. In the case of subject invention constructed from polyurethane foam or other foams, the CNC contour machine would cut completely through the foam to the designed length and width of the intended application, which then would have a vertical and horizontal cut to provide true pressure relief on the intended specific patient. Said device is tapered at sacral and coccygeal area on the anatomical side of the cushion.

Foams of all types and material are specifically polyurethane foams that are formed from stock buns that are used as the raw material for the manufacturing process of the cushion. This cushion device could be formed of another suitable material such as foam, Visco foam, gel, plastic, fiber, rubber, or cotton batting.

The conceptual device was proven to have a utilitarian need and conforming design by making and testing several prototypes. Some of the examples of the prototypes include:

Example 1

A device that incorporates the features of the invention was developed by cutting a piece of polyurethane foam 20"×18"×3" on a programmable hot wire cutting machine, this 20"×18"×3" block of foam is then subject to a second cut on the programmable CNC machine which is programmed to cut entirely through the piece of foam with a vertical cut and a horizontal cut which then represents a cross when removed from the 20"×18"×3" block of foam. The block of foam at this point is subject to a third cutting on the CNC machine and is placed in the programmable CNC machine to have an angle cut on the device 20"×18" this angle cut is then tapered from 3" to 0.75". Angle cut is started 14" from top of cushion and then is tapered to reach 0.75" at bottom of cushion.

The utility and design of the device was demonstrated on a standard size wheelchair.

Example 2

Essentially the same device was made as in example 1 with the exception of the density of foam was significantly higher than the first example. This created a firmer, denser device to support an anatomically larger framed patient/person.

Example 3

This device was cut in same form as that in the first example excepting the size approximately 21"×84"×5" tapering to 3" to height at bottom end of foam piece which was more conducive to be used on patients on the operating room table, MRI, CT, or X-Ray procedure.

A back cushioning device that is comfortable for the purpose of providing true pressure relief and pressure redistribution properties on the entire 5 regions of the spine in those individuals who are compromised with a medical condition or deformity. The said device would have a vertical cut and a horizontal cut. A cushioning device that is tapered at the sacral and coccygeal area of the said device allowing individual to conform back into the device and not feel as if propelled forward. A cushioning device that would be designed to allow situations of positioning as in lying and sitting to offload the entire spine and provide pressure redistribution.

A back cushioning device, wherein a device is vertically cut through and removed to allow the spine of the human anatomy to freely float without pressure on the spine.

A back cushioning device, wherein a device is cut a second time in a horizontal cut through and removed to allow cushion to conform and contour to the entire back area.

A back cushioning device, wherein a device is tapered on the anatomical side of said device at the sacral and coccygeal area.

A back cushioning device that is comfortable for the purpose of providing true pressure relief for the spine and pressure redistribution of tissue load to the back and scapula areas. Said device would be made to encompass the neonatal, pediatric, adult, and bariatric population.

A back cushioning device, wherein the device comprising of a removable vertical cut that would range from 0.5 inch to 8 inches wide by 5 inches to 24 inches long by 1 inch to 8 inches deep, most preferably cut to a width of 4 inches wide by 18 inches long by 3 inches deep.

A back cushioning device, wherein the device comprising of a horizontal cut that would range from 2 inches to 40 inches wide by 1 inch to 8 inches high by 1 inch by 8 inches deep, most preferably 12 inches wide by 2 inches high by 3 inches deep.

A back cushioning device 1 is configured for pressure redistribution each of a cervical region, a thoracic region, a lumbar region, a sacral region, and a coccyx region of a spine of an individual with a medical condition or deformity. The back cushioning device 1 comprising: a cushioning support matrix 2 having a first end 3 configured to be disposed adjacent to the cervical region of the individual and a tapered second end 4 configured to be disposed adjacent to the coccyx region of the individual. A vertical channel 5 is formed along a length of the cushioning support matrix 2. The vertical channel 5 is spaced apart from the first end 3 and extending to the second end 4 of the cushioning support matrix 2. The vertical channel 4 is configured to receive the spine of the individual. A horizontal channel 6 formed along a width of the cushioning support matrix. The horizontal channel 6 being perpendicular to the vertical channel 5 and configured to receive a scapula of the individual.

What is claimed is:

1. A back cushioning device that is configured for pressure redistribution for each of a cervical region, a thoracic region, a lumbar region, a sacral region, and a coccyx region of a spine of an individual with a medical condition or deformity, the back cushioning device comprising:
    a cushioning support matrix having a first end configured to be disposed adjacent to the cervical region of the individual and a tapered second end configured to be disposed adjacent to the coccyx region of the individual;
    a vertical channel formed along a length of the cushioning support matrix and through an entire depth of the cushioning matrix, the vertical channel spaced apart from the first end and extending to the second end of the cushioning support matrix, the vertical channel configured to receive the spine of the individual; and
    a horizontal channel formed along a width of the cushioning support matrix and through an entire depth of the cushioning matrix, the horizontal channel being perpendicular to and intersecting the vertical channel, wherein the horizontal channel is configured to receive at least a portion of a scapula of the individual, and
    wherein the vertical channel has a cervical portion, an intersecting portion, and a thoracic-lumbar-sacral portion, the intersecting portion disposed at an intersection of the horizontal channel with the vertical channel, the cervical portion disposed on a first side of the intersecting portion adjacent the first end of the cushioning support matrix, and the thoracic-lumbar-sacral portion disposed on a second side of the intersecting portion adjacent the second end of the cushioning support matrix, the cervical portion configured to receive at least a portion of the cervical region of the spine of the individual and the thoracic-lumbar-sacral portion configured to receive at least a portion of each of the thoracic region, the lumbar region, and the sacral region of the spine of the individual,
    wherein a length of the vertical portion is at least twice as long as a length of the horizontal portion, and a length of the thoracic-lumbar-sacral portion is greater than a length of the cervical portion,
    whereby the spine of the individual is offloaded by the vertical channel when the individual is lying or sitting on the cushioning support matrix.

2. The back cushioning device of claim 1, wherein the cushioning support matrix includes a member selected from a group consisting of polyurethane foam, viscoelastic foam, poly vinyl foam, natural and synthetic rubber, gel, air, and polyester fiber.

3. The back cushioning device of claim 1, wherein the vertical channel has a width from about 0.5 inch to 8 inches.

4. The back cushioning device of claim 1, wherein the vertical channel has a depth from about 1 inch to 8 inches.

5. The back cushioning device of claim 1, wherein the horizontal channel has a width of about 1 inch to 8 inches.

6. The back cushioning device of claim 1, wherein the horizontal channel has a depth from about 1 inch to 8 inches.

7. The back cushioning device of claim 1, wherein the horizontal channel is disposed closer to the first end of the cushioning matrix than the second end of the matrix.

8. The back cushioning device of claim 1, wherein the vertical channel is disposed centrally on the cushioning matrix.

9. The back cushioning device of claim 1, wherein the cushioning matrix is symmetrical.

10. The back cushioning device of claim 1, wherein the tapered end is tapered for a majority of a depth of the cushioning matrix.

11. The back cushioning device of claim 1, wherein the tapered end is tapered from a first height of 5" to a second height of 3".

12. The back cushioning device of claim 1, wherein the tapered end is tapered from a first height of 3" to a second height of 0.75".

* * * * *